United States Patent
Cooper et al.

(10) Patent No.: US 12,171,501 B2
(45) Date of Patent: Dec. 24, 2024

(54) SYSTEM AND METHOD FOR REVISION HIP SURGERY

(71) Applicant: Simplex Designs, LLC, Duluth, GA (US)

(72) Inventors: Andrew J. Cooper, Belleair Bluffs, FL (US); Noah Wollowick, Belleair Bluffs, FL (US)

(73) Assignee: SIMPLEX DESIGNS, LLC, Cheyenne, WY (US)

( * ) Notice: Subject to any disclaimer, the term of this patent is extended or adjusted under 35 U.S.C. 154(b) by 0 days.

(21) Appl. No.: 17/831,574

(22) Filed: Jun. 3, 2022

(65) Prior Publication Data
US 2023/0010852 A1  Jan. 12, 2023

Related U.S. Application Data

(60) Provisional application No. 63/220,866, filed on Jul. 12, 2021.

(51) Int. Cl.
*A61B 34/20* (2016.01)
*A61B 17/17* (2006.01)
*A61B 34/10* (2016.01)

(52) U.S. Cl.
CPC .......... *A61B 34/20* (2016.02); *A61B 17/1742* (2013.01); *A61B 2034/105* (2016.02)

(58) Field of Classification Search
CPC .............. A61B 17/1742; A61B 17/175; A61B 17/1753; A61B 2034/102; A61B 34/20
See application file for complete search history.

(56) References Cited

U.S. PATENT DOCUMENTS

| | | | |
|---|---|---|---|
| 11,191,651 B1 | 12/2021 | Rivera, Jr. | |
| 2018/0014891 A1* | 1/2018 | Krebs | A61B 5/055 |
| 2018/0221171 A1 | 8/2018 | Termanini et al. | |
| 2020/0074748 A1 | 3/2020 | de Almeida Barreto et al. | |
| 2020/0188026 A1 | 6/2020 | de Souza et al. | |
| 2021/0353431 A1* | 11/2021 | Wilde | A61B 34/20 |
| 2021/0353432 A1 | 11/2021 | Rivera, Jr. | |
| 2022/0125591 A1 | 4/2022 | Rivera, Jr. | |

FOREIGN PATENT DOCUMENTS

WO   2015/089118 A1   6/2015

OTHER PUBLICATIONS

International Search Report and Written Opinion mailed on Oct. 28, 2022, in corresponding PCT/US22/34221, 9 pages.

* cited by examiner

*Primary Examiner* — Samuel S Hanna
(74) *Attorney, Agent, or Firm* — XSENSUS LLP

(57) ABSTRACT

A system and method for identifying and digitally displaying a femoral implant during hip revision surgery to guide a surgeon in detaching the femoral implant from the femur. Some embodiments include digitally registering a portion of the exposed femoral implant to create a representative point set. The system then digitally overlays a medical image of the implant and/or a 3-dimensional model of the femoral implant. Some embodiments further include a surgical tracking system configured to track a surgical cutting tool. Moreover, the system visually illustrates the cutting path of the surgical tool to convey to the surgeon where the surgeon has already cut and where the surgeon needs to cut in order to fully detach the femoral implant from the bone.

6 Claims, 18 Drawing Sheets

106

```
┌─────────────────────┐
│  Initiate validation │
│      procedure      │
│         106a        │
└─────────────────────┘
           │
           ▼
┌───────────────────────────────────────────────────┐
│ Identify the size, orientation, and/or location of the │
│ distal working end of the digital registration tool │
│        relative to the tracking marker(s)         │
│                      106b                         │
└───────────────────────────────────────────────────┘
           │
           ▼
┌───────────────────────────────────────────────────┐
│ Identify the size, orientation, and/or location of the │
│ distal working end of the surgical cutting tool relative │
│            to the tracking marker(s)              │
│                      106c                         │
└───────────────────────────────────────────────────┘
```

Fig. 1C

SYSTEM AND METHOD FOR REVISION HIP SURGERY

CROSS-REFERENCE TO RELATED APPLICATIONS

This nonprovisional application claims priority to provisional application No. 63/220,866, entitled "SYSTEM AND METHOD FOR PERFORMING REVISION HIP REPLACEMENT SURGERY," filed Jul. 12, 2021 by the same inventors.

BACKGROUND OF THE INVENTION

1. Field of the Invention

This invention relates, generally, to implant revision surgery. More specifically, it relates to a surgical navigation system and method for performing implant revision surgery, such as hip revision surgery.

2. Brief Description of the Prior Art

Revision hip replacement surgery (a.k.a. "hip revision surgery") is a surgery in which a previously implanted femoral implant must be surgically removed and replaced. While revision hip surgery is difficult and dangerous, it is a necessity. The life of an artificial hip implant is typically less than 15 years. In addition, excessive wear, dislocation issues, and infections can require revision surgery sooner than the expected life of the implant. As a result, revision surgery often cannot be avoided.

As previously stated, revision surgery is difficult and dangerous. This is because the femoral implant is inserted into a bore within the femur, and after some time, the femur will grow around and on the femoral implant, which is referred to as osseointegration. Effectively, the femoral implant becomes fused to the femur. Once this occurs, the bone must be forcefully disconnected from the femur.

The process for detaching the femoral implant from the femur can take several hours and sometimes results in the accidental shattering of the femur or intentional severing of a section of the femur. Both the accidental shattering and intentional severing of a section of the femur have immensely negative impacts on the patient and can result in death. Thus, it is crucial to minimize the risk of shattering and severing the femur.

Conventional revision hip surgery includes the surgeon removes the ball component from the trunnion on the femoral implant. The surgeon can then initiate the arduous process of detaching the femoral component of the implant from the femur. This process is typically performed with a surgical chisel and requires the surgeon to hammer the chisel between the femoral implant and the femur.

Inherently, there is a lack of precision when hammering a chisel between an implant and an internal bore in a bone, especially when considering that there is a vast number of differently shaped femoral implants and not every chisel is configured to precisely follow the shape of the implant. Furthermore, the surgeon at some point will lose a direct line of sight of the distal end of the chisel when hammering the chisel between the femoral implant and the femur. As a result, during the operation, it is difficult for a surgeon to know: (1) the location of the chisel at any given time with respect to the femoral implant; (2) the location of the chisel at any given time with respect to the outer surface of the femur; (3) where exactly the surgeon has already chiseled away the connection between the femur and the femoral implant; and (4) where exactly the surgeon must chisel away the connection between the femur and the femoral implant to completely detach the femoral implant from the femur. These difficulties result in a significant amount of guess work and growing frustration when the femoral implant does not detach when expected. These difficulties can culminate in the accidental shattering or intentional severing of a section of the femur.

Accordingly, what is needed is a system and method to detach a femoral implant more efficiently and effectively from a femur. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions, or is known to be relevant to an attempt to solve any problem with which this specification is concerned.

BRIEF SUMMARY OF THE INVENTION

The long-standing but heretofore unfulfilled need for a system and method to detach a femoral implant more efficiently and effectively from a femur is now met by a new, useful, and nonobvious invention.

The novel method for removing a femoral implant from a patient's femur includes removing a ball component from the femoral implant implanted in a patient's femur and attaching or digitally registering a coordinate origin marker to a trunnion of the femoral implant. In some embodiments, the coordinate origin marker is secured or digitally registered to a portion of the exposed femoral implant rather than the trunnion of the femoral implant.

The novel method further includes digitally registering an exposed section of the femoral implant to create a point set representative of an outer surface of the exposed section of the femoral implant. In some embodiments, digitally registering the exposed section of the femoral implant includes digitally registering an anterior border of the implant; digitally registering a posterior border of the implant; digitally registering a lateral border of the implant; digitally registering a medial border of the implant; digitally registering a stem collar of the implant; and digitally registering the trunnion of the implant. In some embodiments, the representative point set is created by digitally meshing point sets originating from digitally registering the anterior border, posterior border, lateral border, medial border, stem collar, and trunnion of the femoral implant to create a perimeter of the femoral implant.

The method further includes identifying the characteristics of the femoral implant. In some embodiments, the characteristics include a model of the femoral implant, a size of the femoral implant, an offset value of the femoral implant, and/or a fixation area of the femoral implant.

Once the characteristics are known, a 3D model of the femoral implant based on the identified characteristics of the femoral implant is retrieved. In some embodiments, the 3D model is a geometrically precise representation of the femoral implant corresponding to the identified characteristics.

The 3D model and the representative point set of the femoral implant are overlaid relative to each other. Some embodiments include aligning the 3D model with the representative point set of the femoral implant prior to overlaying the 3D model and the representative point set of the femoral implant relative to each other. Likewise, some embodiments include re-sizing the 3D model based on the size of the representative point set of the femoral implant prior to overlaying the 3D model and the representative point set of the femoral implant relative to each other. Some embodiments further include co-registering the 3D model and the representative point set of the femoral implant relative to each other.

The method further includes tracking a surgical cutting tool relative to the coordinate origin tracking marker using a tracking system. Some embodiments include digitally registering the surgical cutting tool with the tracking system. The surgical cutting tool is also tracked relative to the 3D model. In addition, the tracking system is configured to visually display to a surgeon where future cuts are required to detach the femoral implant from the patient's femur. In some embodiments, real-time tracking data of the surgical cutting tool and the 3D model of the femoral implant are displayed on a graphic user interface. In some embodiments, the surgical cutting tool is tracked relative to a threshold distance from an outer surface of the 3D model and the system alerts a user if the surgical cutting tool meets the threshold distance.

Some embodiments further include securing the surgical cutting tool to a robotic arm. The robotic arm is configured to track the surgical tool relative to the fixation area. Thus, the robotic arm can determine where the cutting tool still needs to cut the implant from the femur.

In some embodiments, the present invention includes a system for aiding in the removal of a femoral implant during revision surgery. The system includes a coordinate origin marker configured to attach to or digitally register to a trunnion of the femoral implant. In some embodiments, the coordinate origin marker is secured or digitally registered to a portion of the exposed femoral implant rather than the trunnion of the femoral implant.

The system further includes a registration probe configured to digitally registering an exposed section of the femoral implant to create a point set representative of an outer surface of the exposed section of the femoral implant. In some embodiments, digitally registering the exposed section of the femoral implant includes digitally registering an anterior border of the implant; digitally registering a posterior border of the implant; digitally registering a lateral border of the implant; digitally registering a medial border of the implant; digitally registering a stem collar of the implant; and digitally registering the trunnion of the implant. In some embodiments, the representative point set is created by digitally meshing point sets originating from digitally registering the anterior border, posterior border, lateral border, medial border, stem collar, and trunnion of the femoral implant to create a perimeter of the femoral implant.

The system also includes a tracking system. The tracking system is configured to track a surgical cutting tool relative to the coordinate origin marker. Some embodiments also include a robotic arm configured to receive the surgical cutting tool.

The system further includes a computer system having a graphic user interface. The computer system is configured to perform the steps of identifying characteristics of the femoral implant; retrieving a 3D model of the femoral implant based on the identified characteristics of the femoral implant; overlaying the 3D model and the representative point set of the femoral implant relative to each other; tracking the surgical cutting tool relative to the 3D model as the surgical cutting tool detaches the femoral implant from the patient's femur; and displaying on the graphic user interface real-time tracking data of the surgical cutting tool and the 3D model of the femoral implant.

In some embodiments, the characteristics include a model of the femoral implant, a size of the femoral implant, an offset value of the femoral implant, and/or a fixation area of the femoral implant. In some embodiments, the computer system further includes a step of digitally registering the surgical cutting tool with the tracking system.

In some embodiments, digitally registering the exposed section of the femoral implant includes digitally registering an anterior border of the implant; digitally registering a posterior border of the implant; digitally registering a lateral border of the implant; digitally registering a medial border of the implant; digitally registering a stem collar of the implant; and digitally registering the trunnion of the implant. In some embodiments, the representative point set is created by digitally meshing point sets originating from digitally registering the anterior border, posterior border, lateral border, medial border, stem collar, and trunnion of the femoral implant to create a perimeter of the femoral implant.

In some embodiments, the computer system further includes a step of aligning the 3D model with the representative point set of the femoral implant prior to overlaying the 3D model and the representative point set of the femoral implant relative to each other. In some embodiments, the computer system further includes a step of re-sizing the 3D model based on the size of the representative point set of the femoral implant prior to overlaying the 3D model and the representative point set of the femoral implant relative to each other. Some embodiments, further include co-registering the 3D model and the representative point set of the femoral implant relative to each other.

BRIEF DESCRIPTION OF THE DRAWINGS

For a fuller understanding of the invention, reference should be made to the following detailed description, taken in connection with the accompanying drawings, in which:

FIG. 1C is a flowchart exemplifying additional procedures for validating the registration of the digital registration tool and the surgical cutting tool with the tracking system.

DETAILED DESCRIPTION OF THE INVENTION

Figure 1A:
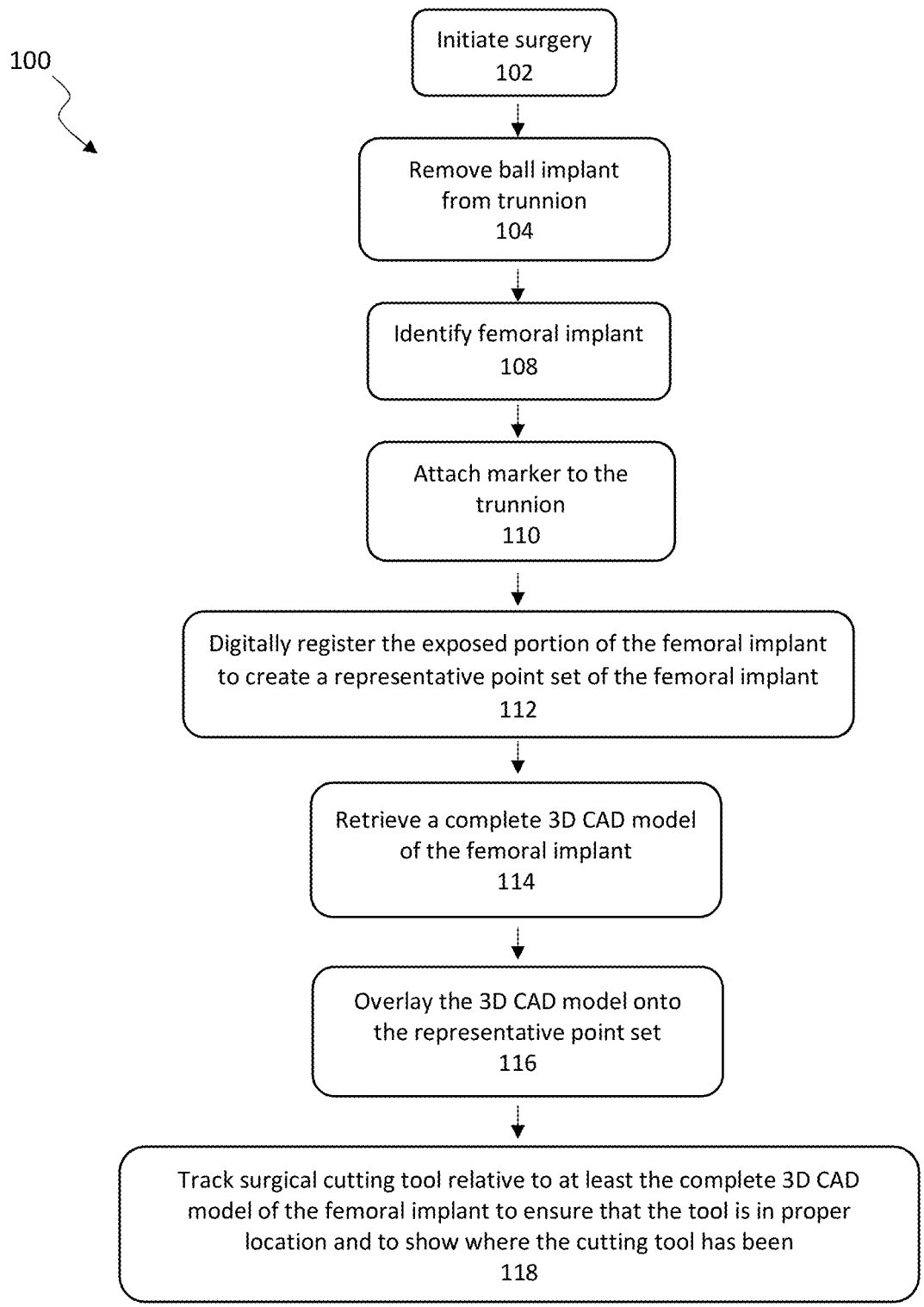
FIG. 1A is a flowchart of an embodiment of the present invention.

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a," "an," and "the" include plural referents unless the content clearly dictates otherwise. As used in this specification and the appended claims, the term "or" is generally employed in its sense including "and/or" unless the context clearly dictates otherwise.

The phrases "in some embodiments," "according to some embodiments," "in the embodiments shown," "in other embodiments," and the like generally mean the particular feature, structure, or characteristic following the phrase is included in at least one implementation. In addition, such phrases do not necessarily refer to the same embodiments or different embodiments.

As used herein, the term "preoperative images" referred to medical images showing the patient's anatomy and/or prostheses prior to an intended surgery. These images may be captured using any medical imaging device, including but not limited to a CT scanner and an X-ray imaging device. These images may be captured through the present invention or may be received or retrieved by the present invention. Moreover, the present invention is adapted to receive the image files in any format including but not limited to .png, .bmp, .jpg, and DICOM format. In some embodiments, the system is configured to access, via a network, one or more databases to retrieve the required images.

As used herein, the term "3D CAD (computer-aided design) model" refers to digital files of 3D designs. 3D CAD models may be any 3D models that include the specific dimensions and/or scale of the corresponding object.

As used herein, the term "tracking system" refers to a system configured to track the movement and location of one or more navigation markers. Some embodiments include cameras and/or sensors that track the position and movement of the markers relative to a coordinate origin point and the associated axes (e.g., X, Y, and Z axes) of a surgical coordinate system. The tracking system may be any known to a person of ordinary skill in the art, including but not limited to, optical tracking systems, RF tracking systems, ultrasonic tracking systems, electromagnetic tracking systems, and/or inertial tracking systems. An exemplary tracking system is NDI's Polaris Vega tracking systems.

The tracking systems are designed to track specific objects and/or navigation markers, which can be physical and/or digital markers. The digital markers are tracked using software adapted to create and register a digital marker on an object and assess the alignment, orientation, movement, and/or position relative to a defined coordinate system.

The physical markers can be active or passive markers designed to allow a sensor to track the alignment, orientation, movement, and/or position relative to a defined coordinate system. The active markers are designed to actively emit some form of energy (e.g., EM waves or radiation) that can be tracked by a particular sensor in a tracking system. The passive markers are configured to react to or reflect energy thereby allowing a predetermined sensor to track said markers. Any markers and sensors known to a person of ordinary skill in the art may be used such that a tracking system can determine the alignment, orientation, movement, and/or position relative to a defined coordinate system.

As used herein, the term "digitally registering," "digitally register," and "registration" refer to a process of identifying the alignment, orientation, and position of an object relative to a defined coordinate system and digitizing the object for use in the tracking system software and for visualization through a graphic user interface. The registration process may be achieved by tracing or outlining an object using a registration tool. The registration tool may be any known to a person of ordinary skill in the art. One example of a registration tool is a pointer tool having a plurality of trackable markers. The surgeon can trace the object with the pointer tool while instructing the tracking software to record the alignment, orientation, movement, and/or position of the tip of the pointer tool relative to a defined coordinate system. Once the object is sufficiently outlined, the tracking software can mesh the recorded points along the outline of the object and digitize the object.

The term "end effector" refers to a surgical instrument that is integrated with or attachable to a robotic arm and is configured to detach an implant from a patient's anatomy. An example of an end effector is a surgical chisel configured to cut through bone growth connecting a femur to a femoral implant residing within the medullary canal of the femur.

The term "surgical cutting tool" refers to a surgical tool configured to detach an implant from a patient's anatomy. An example of a surgical cutting tool is a surgical chisel configured to cut through bone growth connecting a femur to a femoral implant, such as a femoral implant residing within the medullary canal of the femur. End effectors are also examples of surgical cutting tools. In some embodiments, the surgical cutting tool is a 3-sided cutting device configured to cut between the femoral implant and the femur along at least a portion of three different sides of the femoral implant. Non-limiting examples of 3-sided cutting devices include the lateral and medial cutting instruments found in U.S. Pat. No. 11,191,651 and U.S. patent application Ser. Nos. 17/127,006 and 17/387,805. While 3-sided cutting devices are better designed to ride along the sides of the certain femoral implants during cutting process they may still result in the femoral implant failing to detach from the femur. In addition, because 3-sided cutting devices are usually designed to work with specific femoral implants having specific shapes and sizes, these 3-sided cutting devices are less effective for alternative femoral implants for which the cutting devices were not originally designed.

As used herein, the term "fixation area" refers to the area at which an implant is configured or expected to eventually fixate to the patient's anatomy. Some femoral implants will have a portion of their outer surfaces with a texture or material configured to aid in osseointegration. Other implants will simply have a particular size and shape such that a portion of the implant is intended to abut the adjacent bone or is intended to mate to the adjacent bone using an adhesive. Regardless, the fixation area is the area at which the implant is expected to be secured or fixated to the bone. This area can be estimated, identified in the identifiable characteristics of the implant, and/or visualized through medical imaging.

Referring now to the specifics of the present invention, some embodiments, include a system having a memory, a user interface with a visual display, and a processor for executing a program performing at least the steps described herein. In some embodiments, the system is comprised of a plurality of computing devices configured to communicate with each other or with the various devices employed by the present invention. In some embodiments, the present invention is a computer executable method or is a method embodied in software for executing the steps described herein. Further explanation of the hardware and software can be found in the Hardware and software infrastructure examples section below.

The present invention includes a system and method for identifying and digitally displaying a femoral implant during hip revision surgery to guide a surgeon in detaching the femoral implant from the femur in real time. The system includes one or more computer systems and a tracking system. The system of the present invention is configured to digitally register a portion of the exposed femoral implant to create a representative digital point set and digitally overlaying a medical image of the implant and/or a 3-dimensional (3D) model (e.g., a 3D CAD model) of the femoral implant. The system is further configured to track at least a working end of a surgical cutting tool and visually display to a user the past and real-time cutting paths of the surgical cutting tool to convey where the surgeon has already cut and where the surgeon needs to cut in order to fully detach the femoral implant from the bone. In other words, the present invention provides the surgeon with real-time visual information not previously possible during hip revision surgery. This information substantially reduces the time needed to complete a hip revision surgery and drastically reduces the risk of accidentally or purposefully mutilating the femur.

Referring now to the figures, FIG. 1 provides exemplary flow charts of embodiments of the present invention and FIGS. 2-15 provide exemplary user interfaces 200 corresponding to the series of steps in FIG. 1. Upon initiating the surgery at step 102, some embodiments prompt the user to input basic patient information including but not limited to the patient's name in boxes 202 and 204 as exemplified in FIG. 2. Some embodiments further include selectable buttons 206 and 208 to allow a user to identify which hip is the subject of surgery.

At step 104, the surgeon removes the ball implant from the trunnion on the femoral implant. Removing the ball implant is a standard step in hip revision surgery. This step also helps visibly expose more of the femoral implant. In some cases, the exposed portion of the femoral implant will include identifying information thereon thereby supporting or eliminating the need to execute step 108 of identifying the femoral implant. This step will be discussed in greater detail below.

Figure 1B:
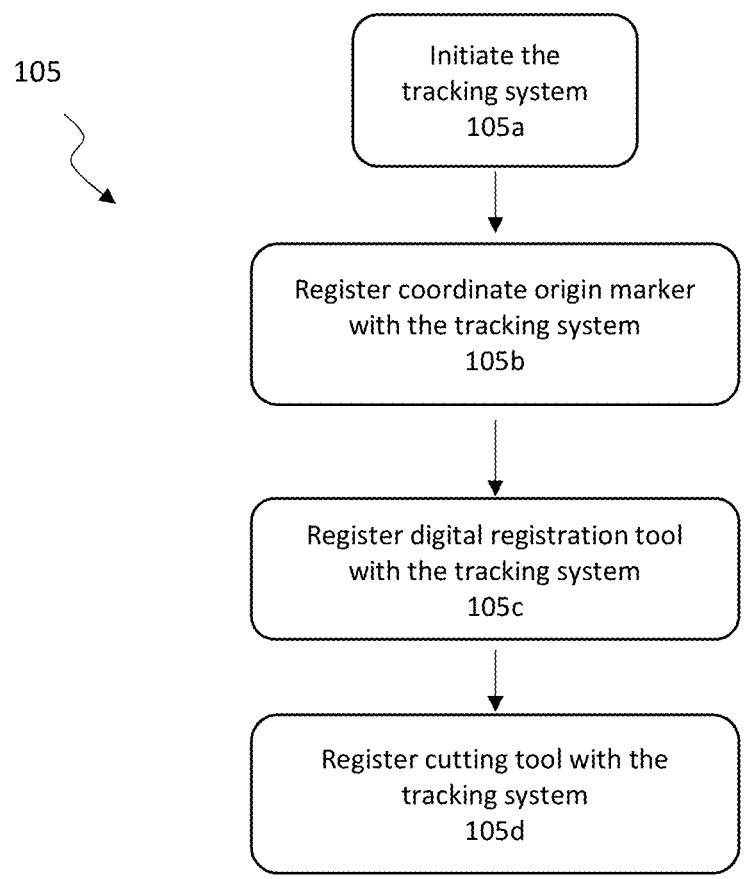
FIG. 1B is a flowchart exemplifying steps for registering various devices with the tracking system.
Figure 2:
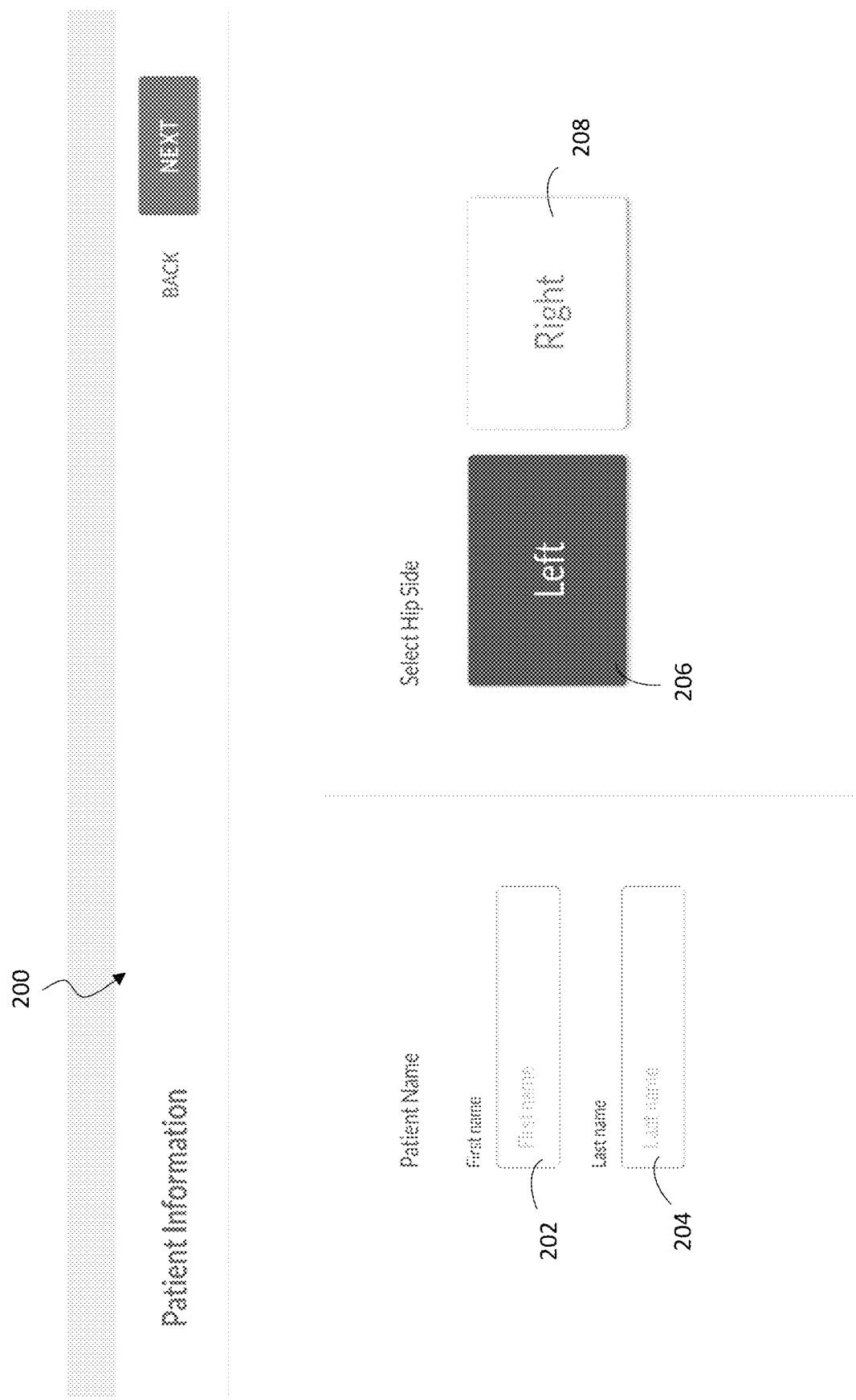
FIG. 2 is an exemplary user interface for inputting patient information.

At this point the tracking system can be setup as exemplified in steps 105 in FIG. 1B if the tracking system has not yet been activated and setup. While steps 105 are described as occurring after the removal of the ball implant, these steps can be performed generally at any point. In most situations, steps 105 will be performed prior to using the surgical cutting tool to separate the implant from the patient's anatomy.

The process of setting up the tracking system includes initiating the tracking system 105a. Once the tracking system is initiated, the coordinate origin marker is registered with the tracking system at step 105b, the registration tool (referred to as "digital probe" in FIGS. 3-4) is registered with the tracking system at step 105c, and the surgical cutting tool is registered with the tracking system at step 105d. Once the various components are registered, the tracking system is configured to identify and track the coordinate origin marker, the digital registration tool, and the surgical cutting tool.

Figure 3:
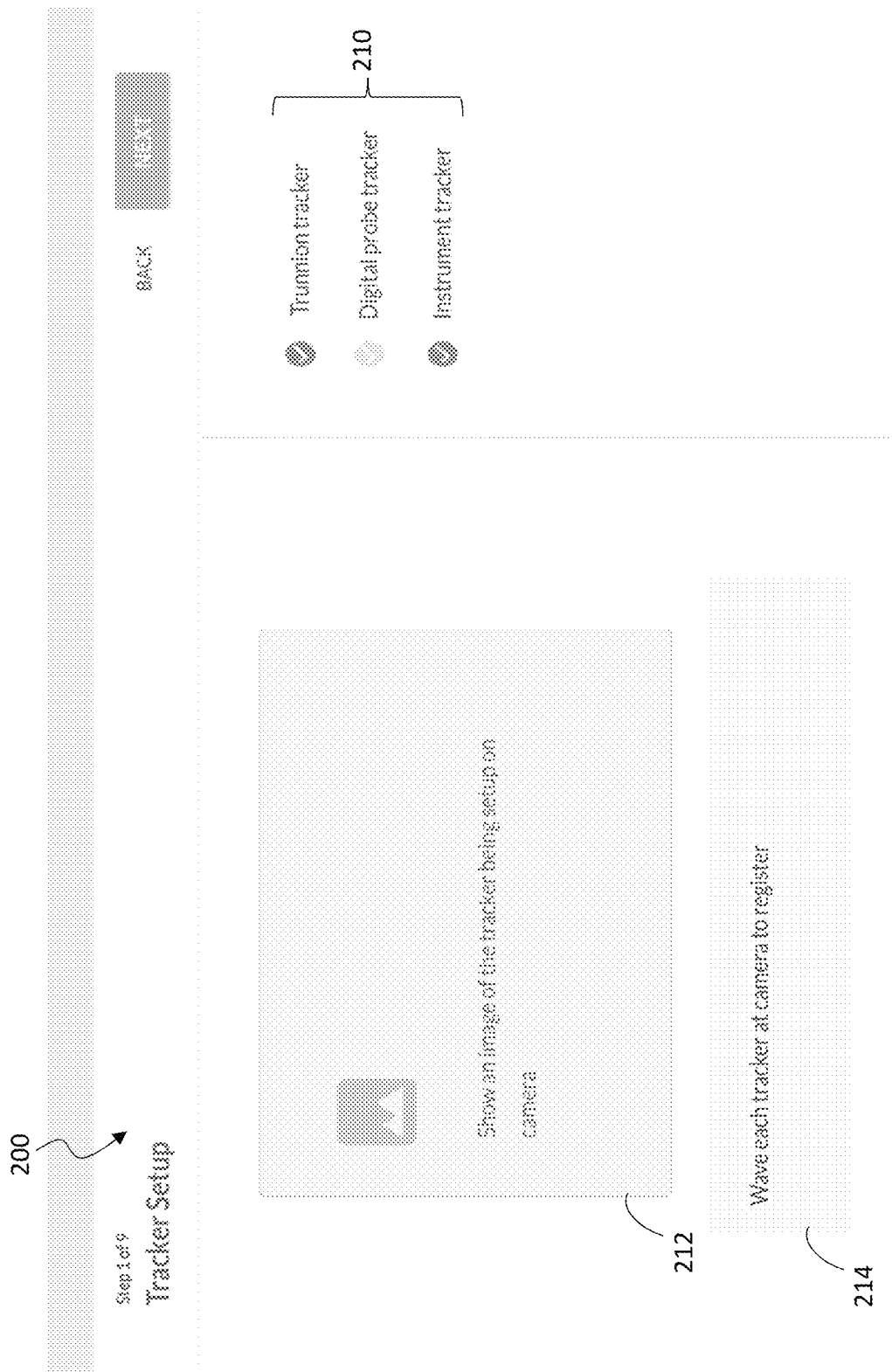
FIG. 3 is an exemplary user interface for the process of registering various devices with the tracking system.

As provided in FIG. 3, the system can display to the user which components were successfully registered with the tracking system using visual indicia 210. In addition, the system can provide visual display 212 of the one or more components after each is registered with the tracking system along with instruction box 214 to guide the user. In some embodiments, the coordinate origin marker, digital registration tool, and surgical cutting tool are provided as a package with the tracking system and each device comes pre-registered with the tracking system.

The digital registration tool and the surgical cutting tool may each require additional validation procedures 106 as exemplified in FIG. 1C to precisely identify the size, orientation, and location of the distal working ends of these devices relative to the corresponding navigation markers on these components. The working ends will not always be visible to the surgeon or the tracking system during the procedure, but some portion of the devices (typically the proximal ends containing the one or more navigation markers) will remain visible. As exemplified in FIG. 1C, the validation procedure is initiated at step 106a. At step 106b, the tracking software identifies the size, orientation, and location of the distal working end of the digital registration tool relative to the navigation markers of the digital registration tool and/or any other markers used by the tracking system including but not limited to the coordinate origin marker. At step 106c, the tracking software identifies the size, orientation, and location of the distal working end of the surgical cutting tool relative to the navigation markers of the surgical cutting tool and/or any other markers used by the tracking system including but not limited to the coordinate origin marker. By validating the instruments, the tracking software can properly convey to the surgeon the location of the working ends of the instruments when the surgeon and tracking software no longer have a visual line of sight of the working ends.

The distal working ends of the surgical cutting tools are generally the cutting portions of the tools. For example, the distal working end of a surgical chisel is the cutting edge or blade portion of the chisel. Thus, the digital registration of the distal working end includes registration of the cutting edge of the chisel. As previously noted, some surgical cutting tools are 3-sided cutting tools and thus the registration of the distal working ends includes registration of the 3 cutting sides proximate the distal working ends of the tools.

Figure 4:
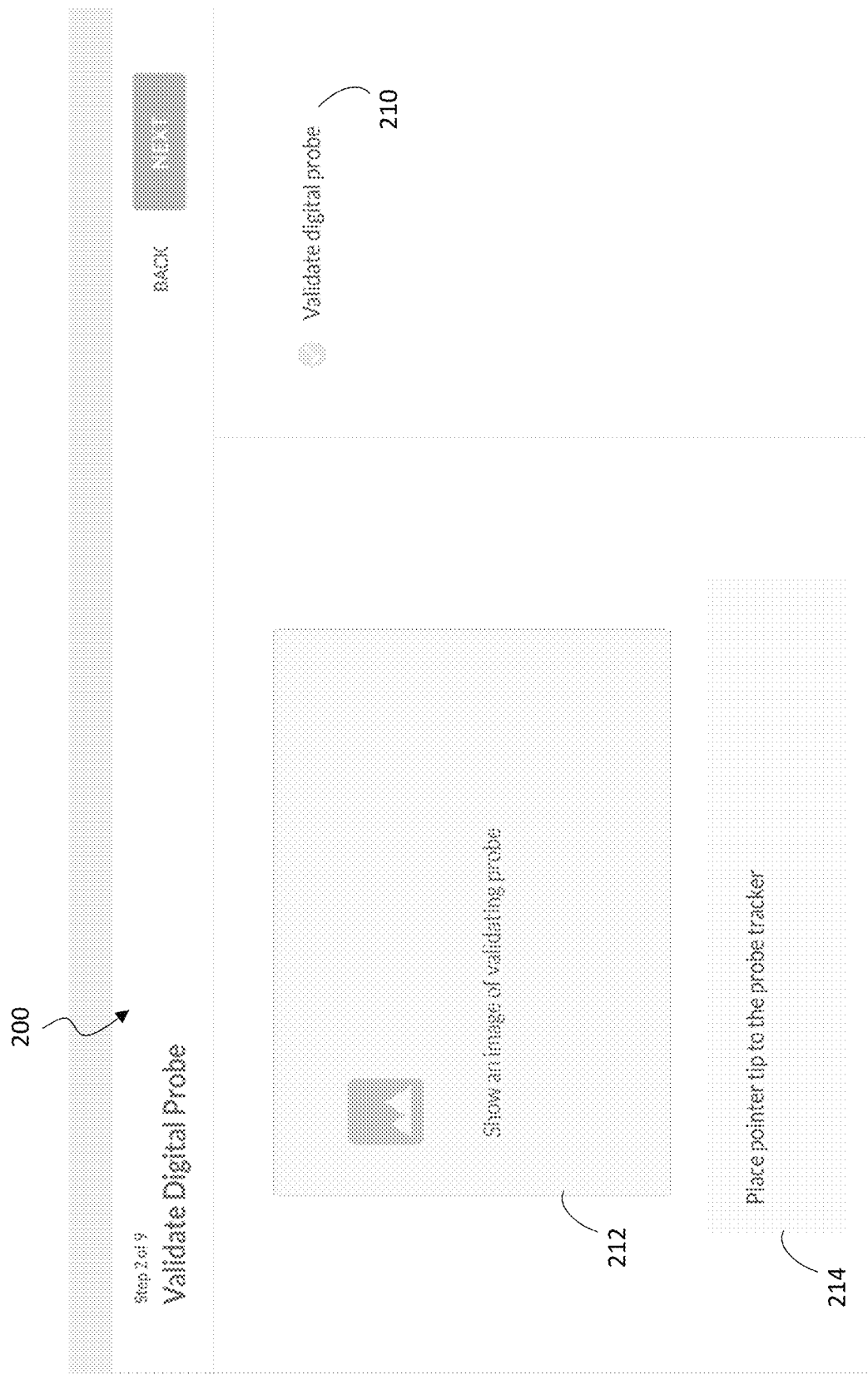
FIG. 4 is an exemplary user interface for the process of validating the registration of the digital registration tool with the tracking system.

As shown in FIG. 4, the validation procedure may be displayed to a user through GUI 200, which can include visual display 212, instruction box 214, and visual indicia 210 for confirming which components were successfully validated. Some embodiments may skip this validation procedure if the tracking system has previously validated the digital registration tool and the surgical cutting tool or if the system comes with a specifically manufactured digital registration tool and surgical cutting tool.

Figure 5:
FIG. 5 is an exemplary user interface for inputting implant information.

As shown in FIG. 5, and during step 108 in FIG. 1, the surgeon is provided with an option to identify the implant and/or the characteristics of the implant. In some situations, the characteristics of the implant (including but not limited to manufacturer, model, size, offset values, and the details of the fixation area) are known. These situations include, but are not limited to, visual identifiable indicia on the implant, information contained in medical records, and a surgeon's personal knowledge of which implant was used. If details of the implant are known or identifiable, the surgeon can input that information.

Figure 6:
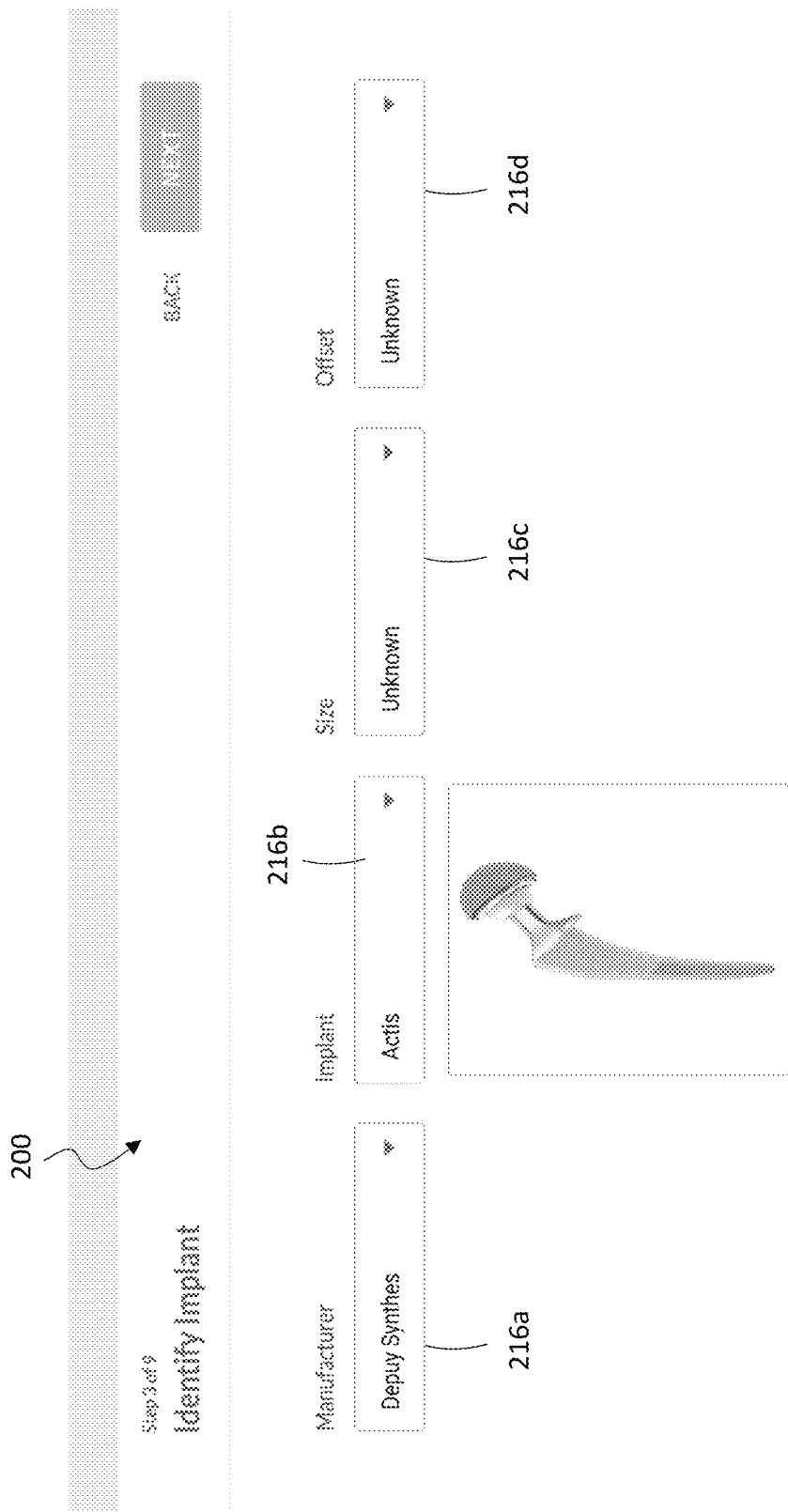
FIG. 6 is an exemplary user interface for inputting implant information and viewing an image of the identified implant.
Figure 7:
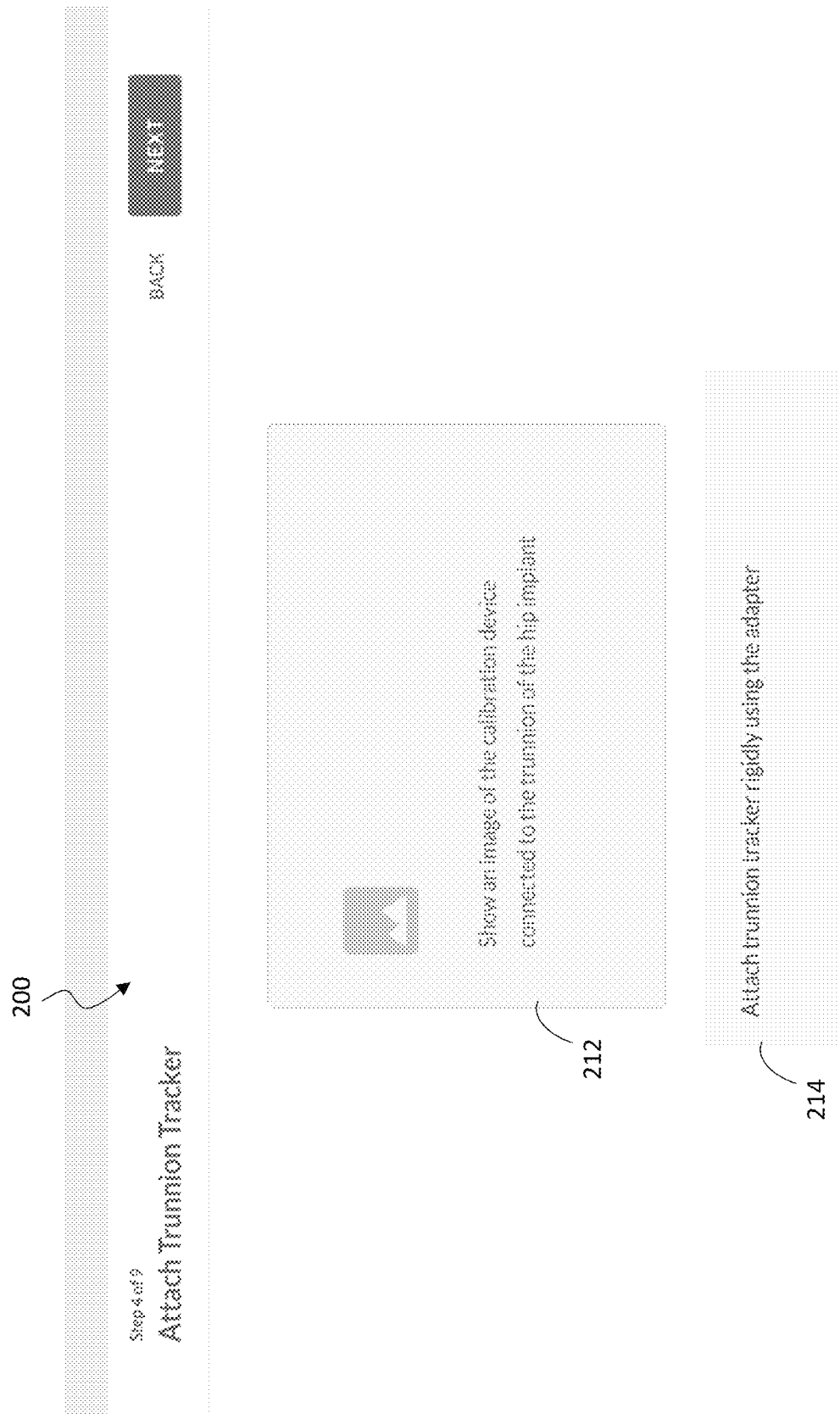
FIG. 7 is an exemplary user interface for attaching the coordinate origin marker to the trunnion.

Some embodiments of the system further include a database of the various implants along with the corresponding manufacturer, size options, offset options, and fixation areas. GUI 200 may include drop down boxes 216 in which the various information can be presented to the user. If enough details are provided, the system can display an image of the implant as shown in FIG. 6.

Referring back to FIG. 1, at step 110, a navigation marker is secured or digitally registered to the trunnion of the implant. In some embodiments, the navigation marker is secured to the free end of the trunnion and may be secured onto the free end via a cap-like component. In some embodiments, the navigation marker is secured to an alternative portion of the exposed femoral implant component. However, securing the navigation marker to the free end of the trunnion ensures that more of the exposed section is available for digital registration and thus identification of the femoral implant.

In some embodiments, the navigation marker attached or digitally registered to the implant is the coordinate origin marker. In some embodiments, the coordinate origin marker is a physical tracker that moves with the implant as the implant moves and rotates during the process of detaching it from the femur. However, some embodiments employ a digital marker with the corresponding software. In addition, more than one navigation marker may be used.

Figure 8:
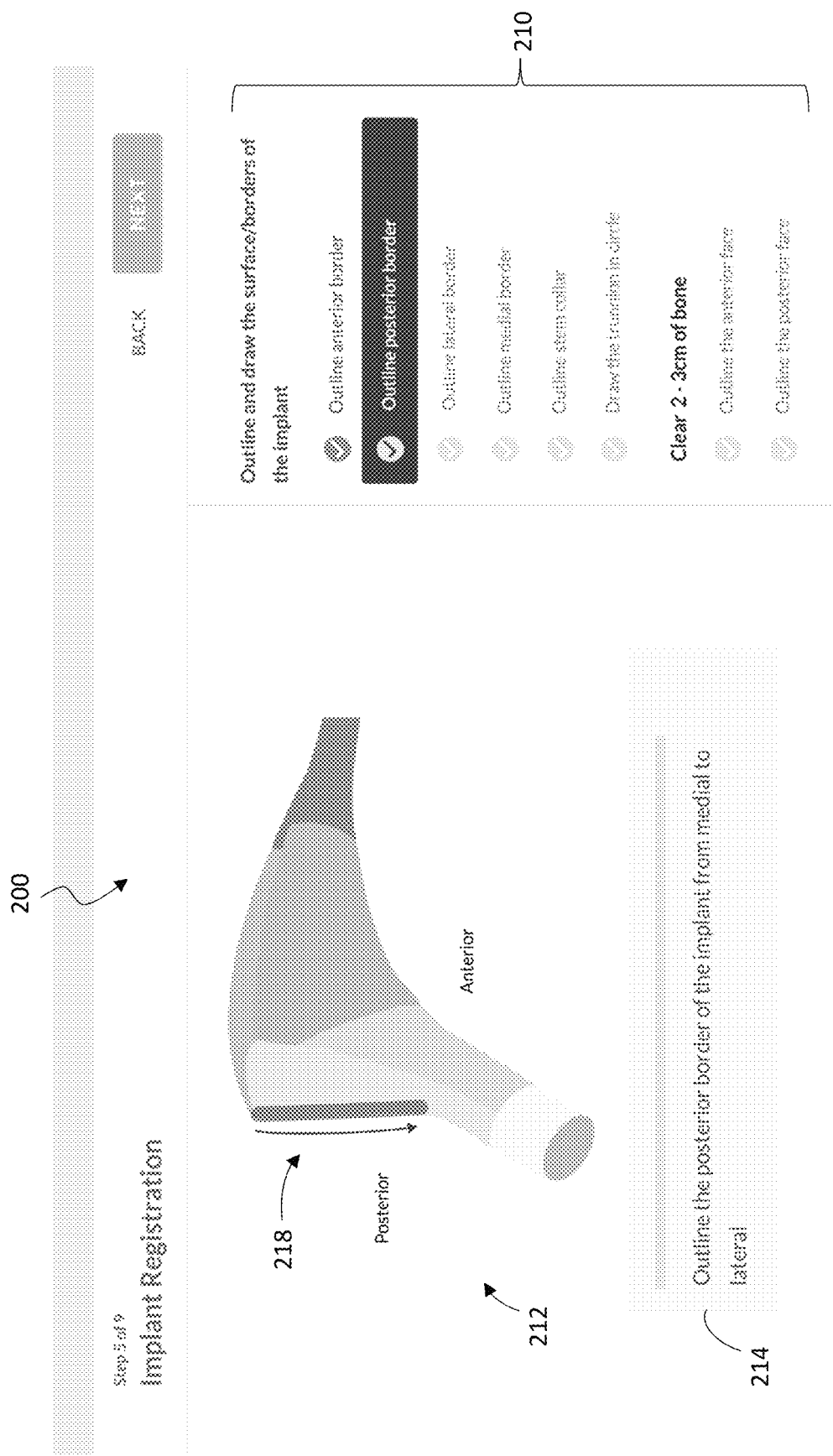
FIG. 8 is an exemplary user interface for the implant registration process.

Referring now to FIGS. 1 and 8, after the coordinate origin marker is secured to the femoral implant, the surgeon digitally registers the exposed portion of the femoral implant at step 112. Because a portion of the stem section of the femoral implant remains exposed after the femoral implant is secured in place during a hip replacement surgery, this same section will generally be exposed during the hip revision surgery. The present invention is able to utilize this exposed section as explained below.

Figure 1D:
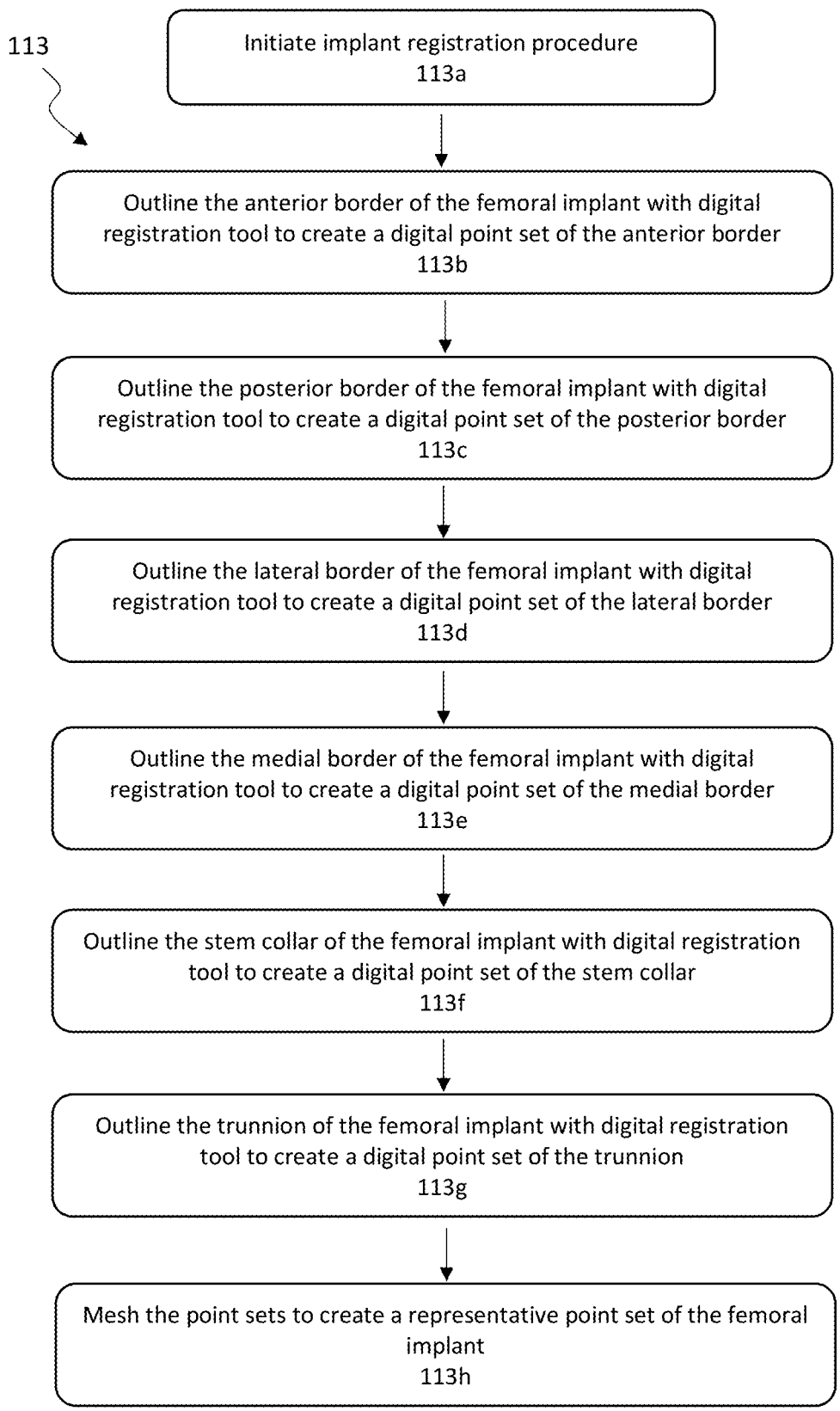
FIG. 1D is a flowchart exemplifying the procedure for digitally registering the various exposed portions of the femoral implant.

As explained in greater detail in FIG. 1D, the registration process 112 includes initiating the implant registration process at step 113a. The digital registration tool is activated and tracked relative to the coordinate origin marker. The surgeon traces the exposed portion of the femoral implant to digitally register a representative point set of the exposed portion of the femoral implant relative to the coordinate origin marker. More specifically, the surgeon traces or outlines the anterior border of the femoral implant at step 113b, the posterior border of the femoral implant at step 113c, the lateral border of the femoral implant at step 113d, the medial border of the femoral implant at step 113e, stem collar of the femoral implant at step 113f, and trunnion of the femoral implant at step 113g. These outlining steps are used to capture point sets, which can then be meshed together to create a digital point set of the exposed area of the femoral implant.

Figure 9:
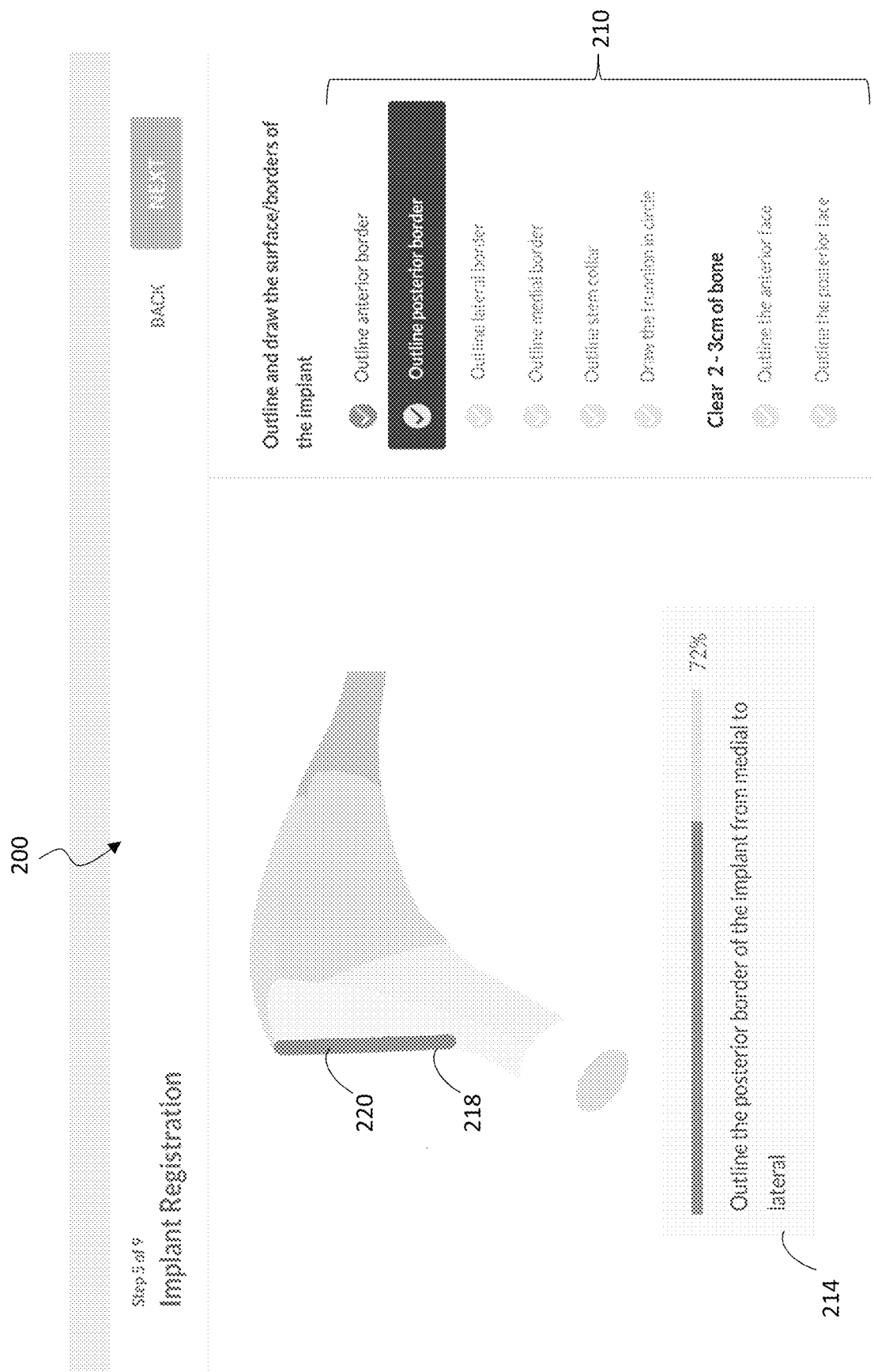
FIG. 9 is an exemplary user interface for the implant registration process depicting the progress of registering the posterior border of the femoral implant.

Some embodiments visually display the digital registration tool and a representative femoral implant on GUI 200 as illustrated in FIGS. 8-9. The tracking system tracks the digital registration tool and GUI 200 visually displays what sections have been registered and/or what sections have not been registered to help guide the surgeon. Some embodiments use color-coded mapping and tracing to guide the surgeon more easily.

Some embodiments do not include a representative femoral implant, but instead display the representative digital point set of the femoral implant as the sections of the implant are digitally registered. The coordinate origin marker is identified as the trunnion and the system digitally adds the point set for traced femoral implant starting at the trunnion and expanding downward.

Referring now to FIG. 8, in some embodiments, GUI 200 includes visual display 212 with instructional graphics/indicators 218 and visual indicia 210 for directing the surgeon during the outlining of the various aspects of the implant. While the form of instructional graphics/indicators 218 is depicted as an indicator line, alternative visual indicators can be used.

As exemplified in FIG. 9, some embodiments also provide a real-time digital completion indicator 220 depicting the current state of the outlining step. In FIG. 9, the completion indicator 220 is exemplified as a different colored line overtop of indicator line 218. However, completion indicator 220 may be an alternative design. The combination of completion indicator 220 and instructional indicator 218 provides the surgeon with a real-time visual indication of the surgeons progress. In some embodiments, the system outputs a completion percentage for the registration of each required surface/border.

Some embodiments also include a step of further exposing the uppermost proximal end of the implant to provide additional points of registration. This can be accomplished by cutting away a limited amount (e.g., 2-3 cm) of bone/tissue using a surgical cutting tool. This additional step allows the surgeon to digitally register the additional revealed features of the femoral implant to increase the odds of successfully identifying the femoral implant.

Referring back to FIG. 1A, once the exposed section of the femoral implant is completely or sufficiently digitally registered to create a point set that generally represents the surface of the exposed section of the femoral implant, the system retrieves the 3D model for the known femoral implant at step 114. In some embodiments, the 3D model is a geometrically precise representation of the femoral implant corresponding to the identified characteristics.

The system can then mathematically fit/co-register the 3D model onto the point set that generally represents the surface of the exposed section of the femoral implant at step 116. The mathematical approach may be any known algorithm or mathematical approach to fit/co-register a 3D model to a point set, including but not limited to the iterative closest point cloud algorithm.

Some embodiments may access a reference library (i.e., a data store) of 3D models for femoral implants ("reference femoral implants") to find a 3D model that precisely matches the point set that generally represents the surface of the exposed section of the femoral implant. The reference library may be stored locally or accessed via a network. The system performs comparative analytics to determine if one or more reference femoral implants match the point set that generally represents the surface of the exposed section of the femoral implant. If an exact match is determined, the system uses that 3D model.

If an exact match is not found, the system performs statistical analysis to determine if any of the reference femoral implants meet a predetermined threshold for confidently matching the representative point set of the exposed femoral implant. The statistical analysis may be performed through any known mathematical approaches. In some embodiments, the predetermined threshold is a statistical correlation equal to or greater a 95% chance of an exact match.

If a match is not identified, the system issues an alert and instructs the surgeon to reperform the steps for digitally registering the exposed section of the femoral implant. Some embodiments also instruct the surgeon to remove more bone to expose and register more of the femoral implant.

Some embodiments may include capturing a medical image or retrieving a preoperative medical image of the surgical site if an exact match is not found in an attempt to capture additional structural data corresponding to the femoral implant. The additional structural data can be used instead of or combined with the data retrieved during the digital registration of the exposed section of the femoral implant.

Some embodiments may use one or more preoperative images as a way to confirm that the digital registration was performed accurately. In determining if the digital registration of the exposed section of the femoral implant was properly performed, the preoperative image may be overlaid onto the digital registration, or vice versa.

Some embodiments may use one or more preoperative images as a way to identify the femoral implant. The surgeon or system may be able to identify structural data which can be employed to identify the femoral implant. Some embodiments may use other devices and methods to identify the femoral implant. For example, some embodiments may include the surgeon using calipers to measure certain areas or features of the femoral implant, which may be used to identify the implant.

Figure 10:
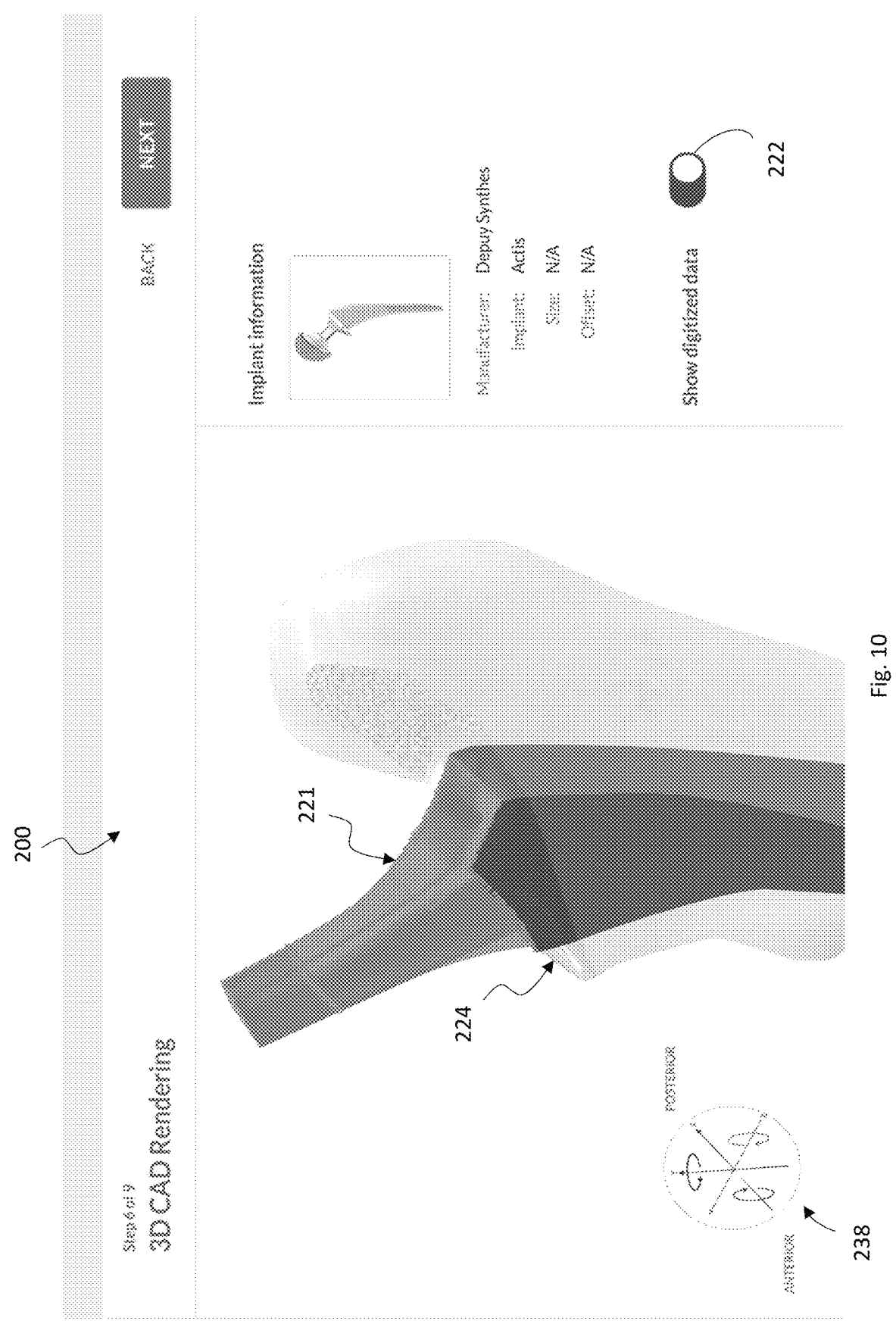
FIG. 10 is an exemplary user interface depicting the overlaid 3D models of the femoral implant.

Regardless of the method used to identify the femoral implant, the system creates a representative point set 221 of the exposed section of the femoral implant. The system retrieves a 3D model (e.g., a CAD model) and overlays 3D model 224 of the entire femoral implant onto the representative point set 221 of the exposed section of the femoral implant (or vice versa) as shown in FIG. 10. The 3D model of the femoral implant may be retrieved from the reference library or from another database. In some embodiments, the 3D model of the femoral implant is created or retrieved from one or more medical images.

Some embodiments further include steps for adjusting the size and orientation of the 3D model of the entire femoral implant relative to the representative point set of the exposed section of the femoral implant, or vice versa. The steps for adjusting the relative size and orientation of the 3D model/representative point set may be performed using any methods and techniques known to a person of ordinary skill in the art.

Once the size and orientation of the 3D model and representative point set are adjusted, as needed, the system co-registers or overlays the 3D model and representative point set. As such, the 3D model and representative point set can be rotated in three dimensions as one. Any methods and techniques known in the art can be used to overlay/co-register the 3D model and representative point set and anchor them to each other for 3D rotation.

In some embodiments, the system displays both the complete 3D model and representative point set of the exposed section of the femoral implant on GUI 200 in visual display 212 and allows a surgeon to toggle the display using digital toggle 222 to show only one as desired. GUI 200 may also display the make, model, and size of the implant.

Figure 11:
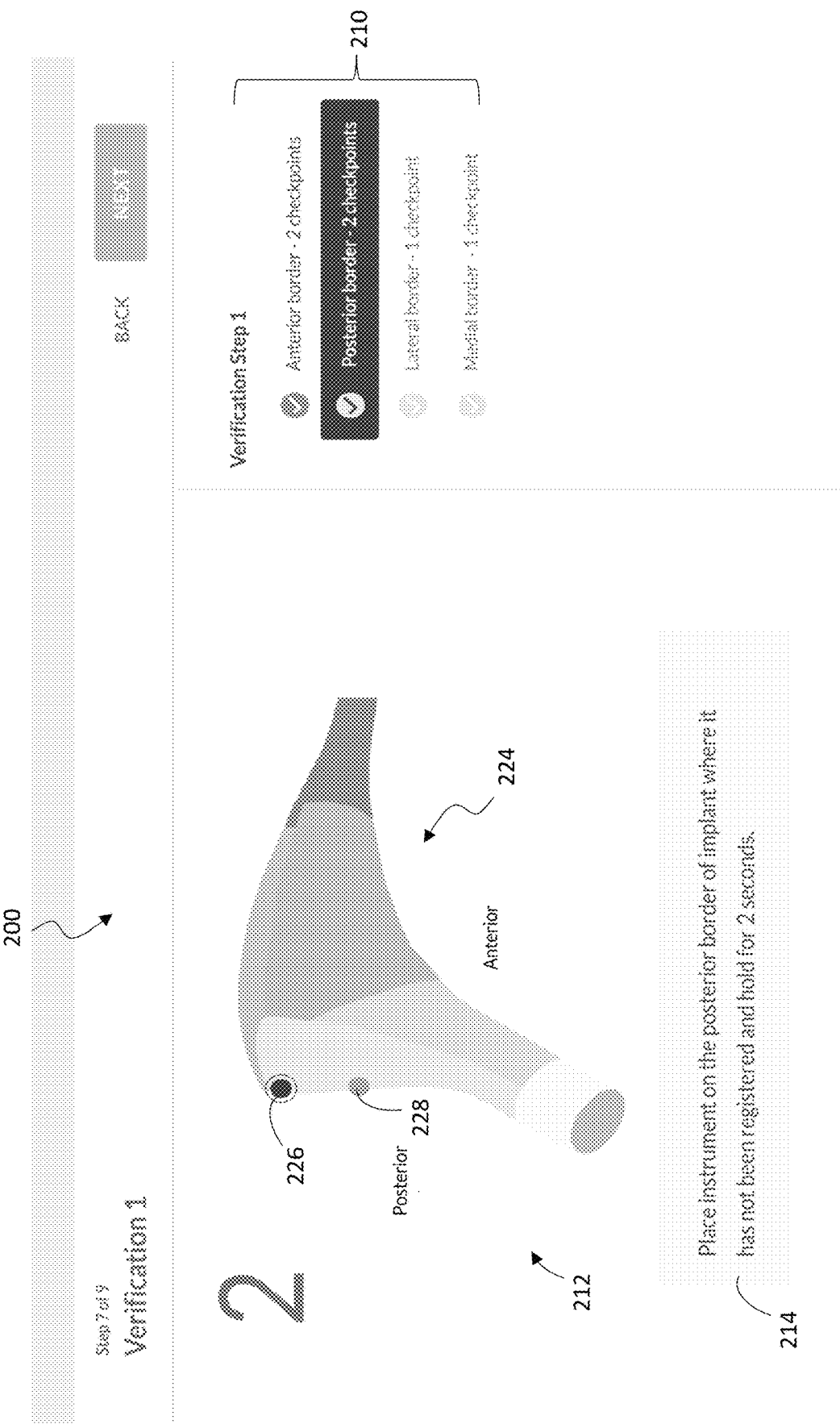
FIG. 11 is an exemplary user interface illustrating an embodiment of a process for verifying that the cutting tool is being properly tracked.
Figure 12:
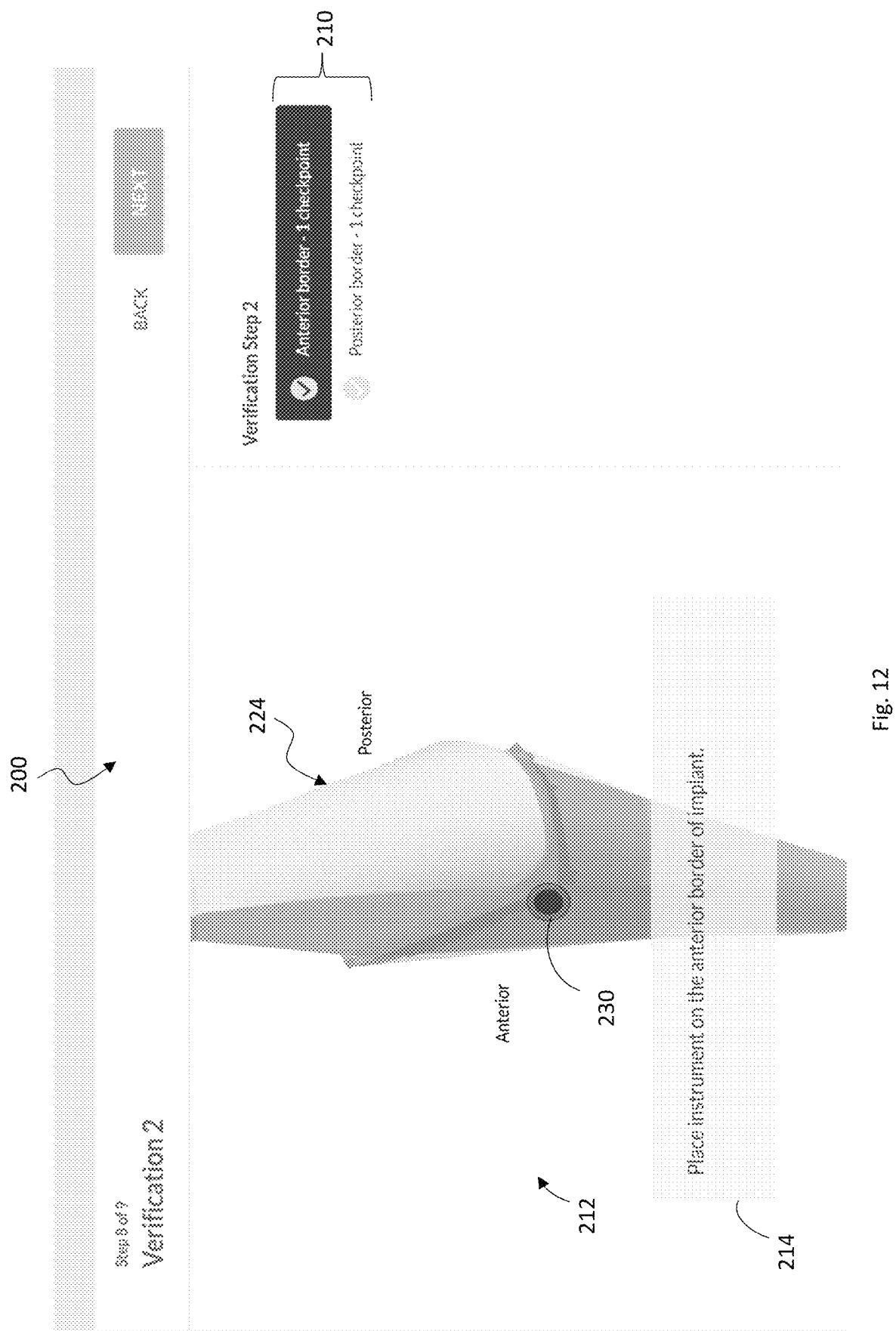
FIG. 12 is an exemplary user interface illustrating an embodiment of a process for verifying that the 3D model accurately represents the femoral implant.
Figure 13:
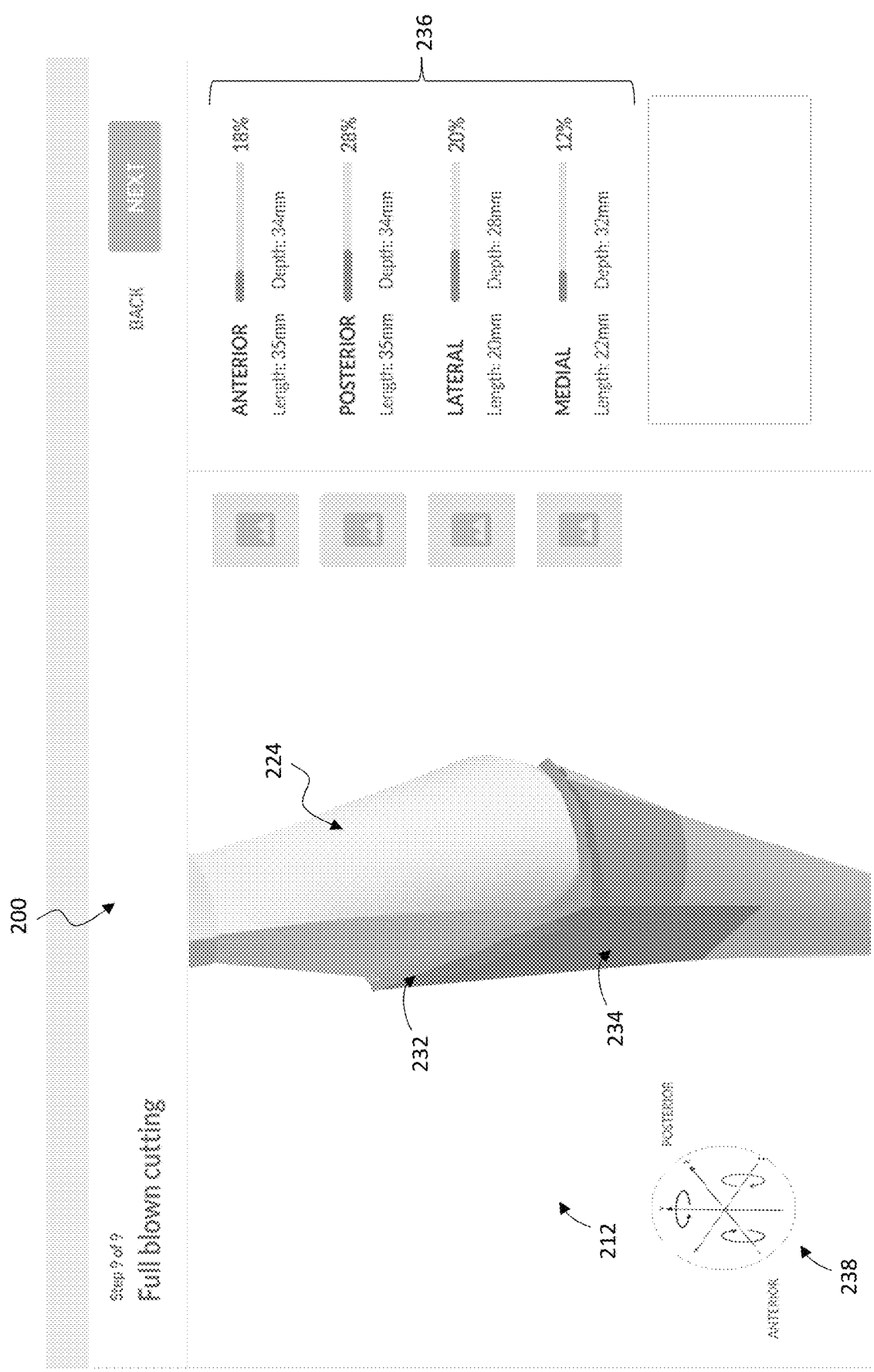
FIG. 13 is an exemplary user interface depicting the surgeon's past cuts relative to areas where the surgeon must continue to cut in order to detach the femoral implant from the femur.
Figure 14:
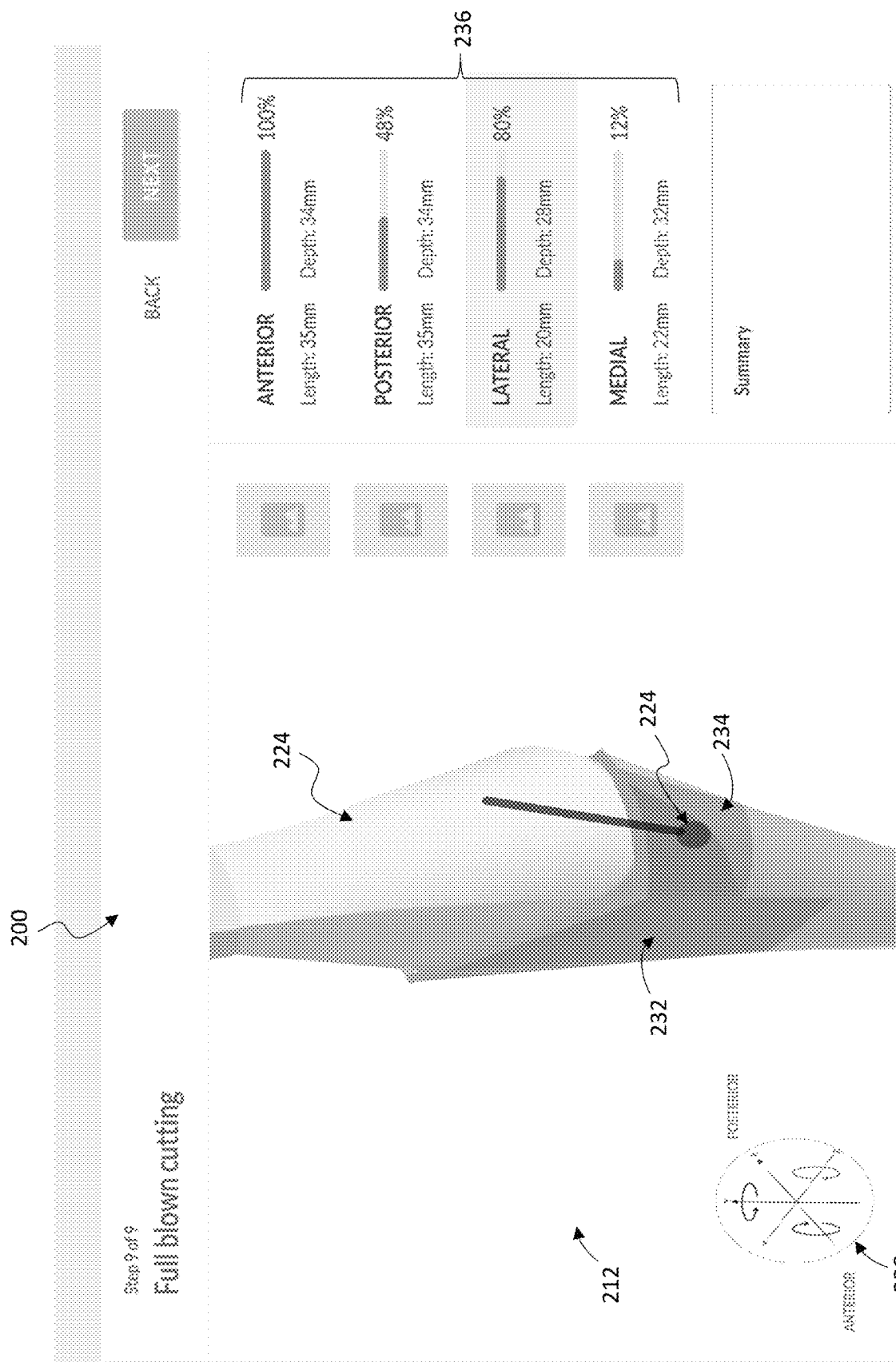
FIG. 14 is an exemplary user interface depicting the location of the cutting tool and where the surgeon previously cut versus where the surgeon must continue to cut in order to detach the femoral implant from the femur.
Figure 15:
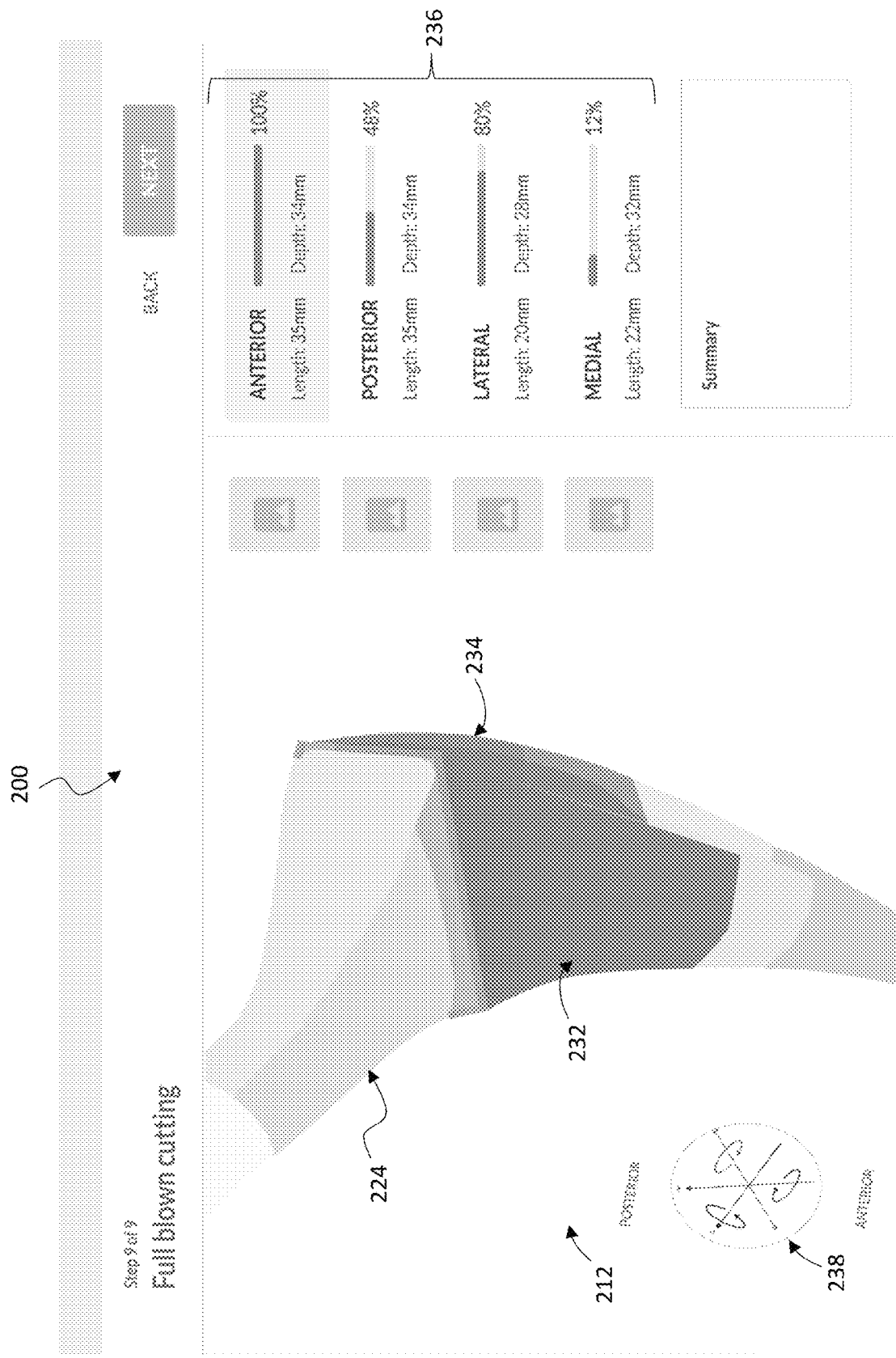
FIG. 15 is an exemplary user interface depicting the ability to rotate the 3D models on the user interface.

In some embodiments, prior to initiating the cutting steps, the system instructs the surgeon to verify the tracking and registration of the cutting tool as sown in FIG. 11. In order to do so, the surgeon touches the distal end of the cutting tool to one or more checkpoints, which can be visually depicted as exemplified by digital checkpoints 226 and 228 in visual display 212. In some embodiments, the surgeon holds the instrument on the one or more checkpoints for a predetermined time. These verification steps can be performed on multiple sides/borders of the implant. The system can then confirm if the cutting tool and/or implant are properly registered such that the distal cutting end is recognized as being located at the checkpoints.

Once the cutting tool and/or implant are properly registered, the surgeon can begin the cutting phase of the surgery for detaching the femoral implant from the femur. Some embodiments include an additional verification step (see FIG. 12) where the surgeon cuts a small, predetermined amount (e.g., 1-3 mm) into the femur and then the system instructs the surgeon to touch one or more verification points 230 (e.g., a point on the anterior border and a point on the posterior border) to validate that the system properly calibrated the size, location, and/or orientation between the 3D model and representative point set. This process may be performed multiple times at different depths.

While the surgeon is cutting, the system tracks the surgical cutting tool relative to the coordinate origin point and in turn the 3D model of the femoral implant. In addition, GUI 200 can display the cutting tool (preferably in a transparent or semitransparent manner) relative to the 3D model of the femoral implant. As the surgeon cuts between the femoral implant and the femur, the tracking system tracks and displays the past and present location of the distal end of the cutting tool as exemplified by digital point 230 in FIG. 14.

The system may identify already cut sections/surfaces from the sections/surfaces that require additional cutting through distinguishable visual indicia, such as colored paths/ surfaces. FIGS. 12-15 provide an exemplary depiction of this feature in which the green area 232 represents already cut areas and the purplish area 234 represents those areas that still need to be cut. Some embodiments also display the depth of the cuts into the femur through display 236, with an estimate on the required depth to detach the femoral implant from the femur.

Some embodiments of the system provide an orientation control element 238, with displayed axes, on GUI 200, which allows the surgeon to manipulate the view as needed. Moreover, some embodiments of the present invention convey the 3D model through an augmented reality system to provide the surgeon with an enhanced visualization of the surgery.

Some embodiments of the present invention may further include boundary lines that extend the length of the femoral implant and are laterally spaced around the femoral implant. These lines establish a safe cutting boundary to guide the surgeon. These boundary lines are preferably visually displayed so that the surgeon can determine when the cutting tool is moving too far in a lateral direction, which could result in catastrophic failure of the femur. Such embodiments may also include alerts to notify the surgeon when the cutting tool is close to, on the boundary, or past the boundary. These alerts may occur in any perceptible form including but not limited to visual, tactile, and/or audible feedback.

Some embodiments of the present invention include a robotic arm coupled to an end effector, such as the surgical cutting tool. The robotic arm is in communication with the tracking system and a computer system configured to use the 3D model and the tracking software to precisely cut the femoral implant from the femur. Such embodiments may include a GUI displaying the digital representation of the cutting procedure similar to FIGS. 13-15.

In some embodiments, the tracking system is used as feedback control software for the robotic arm. In such implementations, the control software uses the identified characteristics of the implant or medical imaging to determine the fixation area (i.e., where the implant is likely secured to the bone) and to what depth the cutting tool must extend to fully detach the implant from the patient's anatomy. By tracking the previous path and estimating the needed path to detach the femoral implant from the patient's anatomy, the control software can direct the robot to cut where necessary to fully detach the femoral implant from the patient's anatomy.

In some embodiments, the robotic arm is tracked in addition to or alternatively with respect to the cutting tool. In addition, the dimensions and orientation of the cutting tool are provided to the system, such that tracking the robotic arm indirectly allows the system to track the cutting tool. Thus, some embodiments include input fields for providing the dimensions and orientation of the cutting tool to the system.

It should be noted that while this application is specifically focused on hip revision surgery and the removal of a femoral implant from a patient's anatomy, the system and method can be used to remove other implants from other areas within a patient. A non-limiting example is shoulder revision surgery in which the present invention aids in removing the humeral stem from the patient.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

Hardware and Software Infrastructure Examples

The present invention may be embodied on various computing systems and/or platforms that perform actions responsive to software-based instructions. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including but not limited to electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C#, C++, Visual Basic or the like and conventional procedural programming languages, such as the "C" programming language or similar programming languages.

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all the generic and specific features of the invention herein described, and all statements of the scope of the invention that, as a matter of language, might be said to fall therebetween.

What is claimed is:

1. A system for aiding in the removal of a femoral implant during revision surgery, comprising:
    a coordinate origin marker configured to attach to or digitally registering to a trunnion of the femoral implant implanted in a patient, wherein the femoral implant has an anterior border, a posterior border, a lateral border, a medial border, a stem collar, and the trunnion;
    a registration probe configured to digitally register an exposed section of the femoral implant to create a point set representative of an outer surface of the exposed section of the femoral implant;
    a tracking system, the tracking system configured to track a surgical cutting tool relative to the coordinate origin marker; and
    a computer system including a graphic user interface and a computer-readable storage medium storing computer-readable instructions thereon, wherein when a processor of the computer system executes the computer-readable instructions, the processor is configured to perform the following steps:
        digitally register, using the registration probe, the anterior border, the posterior border, the lateral border, the medial border, the stem collar, and the trunnion of the exposed section of the femoral implant,
        mesh the digitally registered point sets from each of the anterior border, the posterior border, the lateral border, the medial border, the stem collar, and the trunnion of the exposed section of the femoral implant to create the representative point set;
        identify characteristics of the femoral implant based on information, input by a user, for the femoral implant based on the exposed section of the femoral implant;
        perform comparative analytics to determine whether or not one or more reference femoral implants stored in a database matches the meshed digitally registered point set,
        in a case that match is found, retrieve, from the database, a 3D model of the femoral implant based on the identified characteristics of the femoral implant;
        receive the representative point set from the registration probe;
        in a case a match is not found, determine if any 3D models of femoral implants in the database meet a predetermined threshold for matching the representative point set of the exposed femoral implant,
        overlay the 3D model and the representative point set of the exposed section of the femoral implant relative to each other;
        display, by the graphic user interface, a digital representation of the overlayed 3D model and the representative point set of the exposed section of the femoral implant, wherein the overlayed 3D model and the representative point set of the exposed section of the femoral implant are combined as one in three dimensions;
        track the surgical cutting tool relative to the digital representation of the overlayed 3D model and the representative point set as the surgical cutting tool is used to cut, from the patient's femur, a part of the implant that does not have a point set that has been registered; and
        display on the graphic user interface real-time tracking data of the surgical cutting tool and the 3D model of the femoral implant, wherein the graphic user interface includes boundary lines extending a length of and laterally spaced around the femoral implant, the boundary lines establishing a cutting boundary.

2. The system of claim 1, wherein the characteristics of the femoral implant include a model of the femoral implant, a size of the femoral implant, and an offset value of the femoral implant.

3. The system of claim 1, wherein the processor is configured to digitally register the surgical cutting tool with the tracking system.

4. The system of claim 1, wherein the processor is further configured to align the 3D model with the representative point set of the femoral implant prior to overlaying the 3D model and the representative point set of the femoral implant relative to each other.

5. The system of claim 1, wherein the processor is further configured to re-size the 3D model based on the size of the representative point set of the femoral implant prior to overlaying the 3D model and the representative point set of the femoral implant relative to each other.

6. The system of claim 1, further including a robotic arm configured to receive the surgical cutting tool.

* * * * *